United States Patent [19]  
Costa

[11] 4,316,046  
[45] Feb. 16, 1982

[54] PROCESS FOR THE PREPARATION OF ARYL CARBOXYLATES

[75] Inventor: Lawrence C. Costa, Nanuet, N.Y.

[73] Assignee: The Halcon SD Group, Inc., New York, N.Y.

[21] Appl. No.: 182,529

[22] Filed: Aug. 29, 1980

[51] Int. Cl.$^3$ .............................................. C07C 67/00
[52] U.S. Cl. ........................... 560/130; 260/345.8 R; 260/346.22; 260/347.4; 260/410.5; 260/465 R; 260/465 D; 260/333; 549/52; 549/1; 549/13; 560/51; 560/53; 560/54; 560/84; 560/96; 560/105; 560/129; 560/139; 560/141; 560/142; 560/143; 560/144; 560/146; 560/8; 560/20; 560/71
[58] Field of Search ............... 560/105, 139, 142, 143, 560/144, 146, 96, 84, 51, 53, 54, 129, 141, 130; 549/52; 260/410.5, 345.8 R, 347.4, 346.22, 465 R

[56] References Cited

U.S. PATENT DOCUMENTS

| | | | |
|---|---|---|---|
| 3,574,777 | 4/1971 | Heck | 560/53 |
| 3,700,727 | 10/1972 | Heck | 260/347.4 |
| 3,705,919 | 12/1972 | Heck | 560/54 |
| 3,917,670 | 1/1975 | Baird, Jr. et al. | 260/347.4 |
| 4,182,915 | 1/1980 | Harvey | 568/716 |

FOREIGN PATENT DOCUMENTS 47-10705 3/1972 Japan ..................................... 560/96

Primary Examiner—Howard T. Mars  
Assistant Examiner—Frederick W. Pepper  
Attorney, Agent, or Firm—William C. Long; David Dick; Riggs T. Stewart

[57] ABSTRACT

A process for the preparation of aryl carboxylates is provided in which an arylmetallo carboxylate is contacted with an aryliodoso carboxylate in liquid medium to form the desired aryl carboxylate. Promoters can be employed to increase the rate of reaction and improve selectivity to the aryl carboxylate.

7 Claims, No Drawings

PROCESS FOR THE PREPARATION OF ARYL CARBOXYLATES

CROSS-REFERENCE TO RELATED APPLICATION

This application is related to my co-pending application entitled "Process for the Catalytic Production of Aryl Carboxylates", Application Ser. No. 182,512, filed Aug. 29, 1980.

BACKGROUND OF THE INVENTION

1. Field of the Invention

This invention relates to the preparation of aryl carboxylates and more particularly to the preparation of aryl carboxylates from the corresponding arylmetallo carboxylate.

2. Description of the Prior Art

Aryl carboxylates, such as phenyl carboxylates (e.g., phenyl acetate, phenyl salicylate and the like) find a wide variety of uses. For example, phenyl acetate can be hydrolyzed to prepare phenol, and also finds use as a solvent. Phenyl salicylate is used as a preservative.

Various methods for preparing aryl carboxylates are known. For example, phenyl acetate can be prepared from the reaction of phenol and acetyl chloride or acetic anhydride, or by heating triphenyl phosphine in the presence of potassium acetate and alcohol. See, e.g., *Condensed Chemical Dictionary*, 8th Ed., p. 678 (1971). Also known is a process for preparing aryl carboxylates by reaction of aryl thallium (III) metallates with the corresponding carboxylic acid. See U.S. Patent 4,182,915 (issued in 1980 to R. J. Harvey).

Diaryl mercury compounds are known to react with aryl iodoso dihalides to produce a diaryliodonium halide and an aryl mercuric halide compound. F. M. Beringer, et al., 75 *J. Amer. Chem. Soc.* 2705 (1953). Also known is the reaction of phenyl magnesium chloride with phenyl iodoso dichloride to produce a complex mixture of products which has been variously reported as being only phenyl iodide and diphenyl or a mixture of phenyl chloride, phenyl iodide, diphenyl and diphenyl iodonium chloride. R. B. Sandix, 32 *Chem. Rev.* 249, at 261 (1943).

The use of such diaryl iodonium salts in various synthesis reactions has been reported in a number of references. In addition to the above two articles by Beringer, et al. and Sandix, illustrative literature on this subject includes F. M. Beringer, et al., 75 *J. Amer. Chem. Soc.* 2708 (1953); M. C. Caserio, et al., 81 *J. Amer. Chem. Soc.* 336 (1959); F. M. Beringer, et al., 81 *J. Amer. Chem. Soc.* 342 (1959); and F. M. Beringer, et al., 81 *J. Amer. Chem. Soc.* 351 (1959). Studies of use of diphenyl iodonium salts in hydrolysis reactions show copper (I) and copper (II) to be catalysts for the hydrolysis reaction. The non-catalyzed hydrolysis reaction is suppressed by the presence of acid. The copper catalyzed reaction was also found, in varying degrees, to be retarded by the presence of acid.

Diphenyliodonium bromide has been reacted with sodium benzoate to form phenyl benzoate and phenyl iodide, and the reaction has been found to be faster in strong bases. F. M. Beringer, et al., 75 *J. Amer. Chem. Soc.* 2708 (1963).

SUMMARY OF THE INVENTION

According to the process of this invention, it has been found that aryl metallo carboxylates can be readily reacted in liquid medium with aryliodoso dicarboxylates to form aryl carboxylates in addition to aryl iodides and metallo carboxylate salts.

DETAILED DESCRIPTION OF THE INVENTION

The arylmetallo carboxylates which are useful as reactants in the process of this invention comprise compounds having the formula:

$$R^1{}_n\text{—}M\text{—}X^1{}_m \qquad \text{(I)}$$

wherein $R^1$ is a mono- or polynuclear aryl; M is a metal cation selected from the group consisting of Hg, Sn, Tl, Pb and Cd; $X^1$ is a carboxylate group of from 2 to 20 carbon atoms derived from an aliphatic or aromatic mono- or di-carboxylic acid; and n and m are each integers of from 1 to $(t-1)$, wherein t is the valence of the M metal cation, with the proviso that $n+m=t$.

The metal cations "M" of the foregoing arylmetallo carboxylate reactants will be in their highest respective normal oxidation state. Thus, the valences of the metal cations in the reactants will be as follows: $Hg^{2+}$, $Sn^{4+}$, $Tl^{3+}$, $Pb^{4+}$ and $Cd^{2+}$. Compounds containing any of the foregoing metals in lower valences can be present in the reaction zone and do not interfere with the desired reaction.

The aryl iodoso carboxylates which are useful as reactants in the process of this invention comprise at least one compound of the formula:

$$R^2\text{—}I\diagup^{X^2}_{X^3} \qquad \text{(II)}$$

wherein $R^2$ is mono- or polynuclear aryl, $X^2$ and $X^3$ are the same of different and are each carboxyl groups derived from aliphatic saturated or aromatic monocarboxylic acids having from 2 to 20 carbon atoms, or from aliphatic saturated or aromatic di-carboxylic acids having from 2 to 20 carbon atoms. It will be appreciated that $X^2$ and $X^3$ can comprise the same difunctional moiety as when the moiety is derived from a dicarboxylic acid. For example, aryliodoso dicarboxylates of the formula:

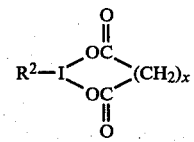

wherein $R^2$ is as defined above, and x is an integer of from 0 to 18, are included within the compounds of the formula (II) above. The carboxylate moieties, $X^1$, $X^2$ and $X^3$ will preferably have from 2 to 6 carbon atoms.

The $R^1$ and $R^2$ aryl groups can be substituted or unsubstituted; and will generally each have a total of from about 6 to 18 carbon atoms, and preferably from about 6 to 14 carbon atoms. When substituted, suitable organic substituents include alkyl of 1 to 12 carbon atoms, cycloalkyl of 4 to 12 carbon atoms, and heterocyclic having from 6 to 10 member rings containing one or more O or S ring atom, cyano, keto having from 2 to 10 carbon atoms, carboxylate having from 1 to 10 carbon atoms, and carboalkoxy having from 2 to 10 carbon atoms. Illustrative of the foregoing organic substituents are methyl, butyl, decyl, cyclobutyl, cyclooctyl, cyclododecyl, furyl, pyranyl, benzofuranyl, benzothiofuranyl, cyano, acetyl, butanoyl, benzoyl, carbomethoxy, carboheptoxy and the like. Suitable inorganic substituents to the $R^1$ and $R^2$ groups include halide (e.g., Cl, F, I and Br), nitro, hydroxy, sulfo and the like.

Illustrative of suitable $R^1$ and $R^2$ aryl groups are phenyl, 2-tolyl, 2,4-xylyl, 3-cyclohexyl phenyl, 4-tolyl, 2-isopropylphenyl, 3-isopropylphenyl, 4-isopropylphenyl, 2-carboxylphenyl, 2-hydroxyphenyl, 2-cyanophenyl, 3-nitrophenyl, 2,3-dichlorophenyl, naphthyl, and the like. Preferred as the $R^1$ and $R^2$ aryl groups in the practice of this invention are phenyl, 2-, 3-, and 4-isopropylphenyl and naphthyl, with phenyl being especially preferred.

The $R^1$ and $R^2$ aryl groups of the arylmetallo carboxylate and the aryliodoso carboxylate reactants can be the same or different. Also, the $X^1$, $X^2$ and $X^3$ carboxylate moieties can be the same or different. Most preferably, the $R^1$ and $R^2$ aryl groups are the same, and $X^1$, $X^2$ and $X^3$ are the same.

Exemplary aliphatic monocarboxylic acids from which such $X^1$, $X^2$ and $X^3$ carboxylate moieties can be derived are branched and straight-chained acids such as acetic, propionic, isobutyric, pentanoic, hexanoic, octanoic, decanoic, and the like, and aryl-substituted derivatives of the foregoing such as phenylacetic acid and the like. Exemplary aliphatic dicarboxylic acids are oxalic, malonic, succinic, glutaric, adipic and the like. Exemplary aromatic carboxylic acids are terephthalic, isophthalic, phthalic and the like.

The foregoing aliphatic and aromatic mono- and di-carboxylic acids can be substituted or unsubstituted, and when substituted can contain such substituents as hydroxy, cyano, keto, carboalkoxy, nitro, halo (e.g., fluoro, chloro and bromo), and the like. Exemplary of such substituted acids, from which the $X^1$, $X^2$ and $X^3$ moieties can be derived, are salicyclic acid, m-chlorobenzoic acid, 4-hydroxybenzoic acid, trifluoroacetic acid and the like.

Therefore, illustrative of suitable arylmetallo carboxylate reactants of this invention are phenylmercuric acetate, triphenyl tin acetate, tolylmercuric acetate, tolyltin triacetate, 4-isopropylphenylthallium diacetate, phenylthallium ditrifluoroacetate and the like.

Illustrative of suitable aryliodoso carboxylate reactants of this invention are phenyl iodoso diacetate, p-tolyliodoso diacetate, phenyliodoso ditrifluoroacetate, 4-methoxyphenyliodoso diacetate, naphthyliodoso di-(ethyl benzoate), and the like.

The foregoing reactants are contacted in accordance with this invention in liquid medium. The conditions of temperature and pressure which are employed in the reaction are not critical and may vary widely. Generally, temperatures of from about 25° to 150° C. will be entirely sufficient, with temperatures from about 50° to 100° C. being more usually employed.

Pressure is not a critical parameter of the process of this invention and the reaction can be run at any convenient pressure, including atmospheric, subatmospheric or superatmospheric pressure. An inert atmosphere is not required and therefore the reaction can be conveniently operated in the presence of air.

The arylmetallo carboxylate and aryliodoso carboxylate reactants of this invention are preferably contacted in a molar ratio of from about 10:1 to 1:10, more preferably from about 1:1 to 1:2. However, these ratios are not critical, it being recognized that the reaction is a stoichiometric one. Therefore, it will be apparent that the use of the aryliodoso carboxylate in an amount less than that which is stoichiometrically required to react with the quantity of aryl metallo carboxylate present in the reaction medium will only limit the yield of aryl carboxylate, based on aryl metallo carboxylate charged.

The reaction is preferably conducted in the substantial absence of strong organic bases, such as pyridine and alkali or alkaline earth metal carboxylates, since these compounds have been found to severely inhibit the formation of the desired aryl carboxylates. For the purpose of this invention, the term "strong organic base" is intended to mean organic compounds which have a base association constant ($K_b$) such that the $pK_b$ (where $pK_b = -\log K_b$) is not greater than $-3.5$, wherein "$K_b$" is determined by the reaction:

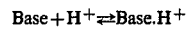

and is defined by the expression:

$$K_b = \frac{[Base \cdot H^+]}{[Base][H^+]}$$

in which [Base]) [Base.H$^+$] and [H$^+$] are the concentrations, in mole/liter, of the basic compound, its associated conjugate acid and H$^+$ ion, respectively, at 25° C.

The reaction time may vary widely, and the reaction will generally be complete after a period of from 0.1 to 6 hours.

The reaction in accordance with the process of this invention is employed in liquid medium. Sutiable solvents include alcohols (e.g., lower alkanols sych as methanol, ethanol, tert-butanol, and the like), ethers (e.g., tetrahydrofuran, dioxane and the like), nitriles (e.g., acetonitrile, benzonitrile, isobutyronitrile and the like), ketones (e.g., acetone, methyl ethyl ketone, acetophenone and the like), amides (e.g., dimethyl formamide, dimethylacetamide, N-methyl-pyrrolidinone, and the like), esters (e.g., esters of lower monocarboxylic acids, such as ethylene glycol diacetate, propylene glycol diacetate, and the like), and carboxylic acids (e.g., any of the carboxylic acids discussed above). Mixtures of organic solvents and water are also suitable. Carboxylic acids, either alone or in combination with water, are especially preferred as liquid media for this reaction.

The process of this invention can be performed in a batchwise, semi-continuous manner, and the manner of contacting the reactants is not critical. Thus, the arylmetallo carboxylate, aryliodoso carboxylate and solvent can be pre-mixed or fed separately to the reaction vessel.

The concentration of the selected arylmetallo carboxylate and aryliodoso carboxylate reactants in the liquid reaction medium is not critical. Preferably, however, the aryl metallo carboxylate and aryliodoso carboxylate are each employed in a concentration such that the sum of their concentrations is at least 0.05, and more preferably from 0.5 to 5.0, moles per liter of liquid reaction medium, to achieve further improved yields and selectivities of the desired aryl carboxylate product.

The reaction to the desired aryl carboxylate can be promoted by employing in the reaction zone an effective amount of at least one metal salt selected from the group consisting of inorganic and organic salts of Cu, Co, Fe and Mn, and mixtures thereof, which is at least partially soluble in the liquid reaction medium. Exemplary of suitable organic promoter salts are the carboxylates of these metals, such as cupric acetate, cupric butyrate, cobalt acetate, manganese acetate, and the like, Exemplary inorganic salts are the halides (such as ferric chloride, cuprous iodide, manganous bromide, cobaltic chloride and the like), sulfates (such as cupric sulfate, ferric sulfate and the like) and nitrates (such as cobaltous nitrate, ferric nitrate and the like).

The quantity of such promoter is not critical, and the promoter will generally be employed in an amount of at least about 0.1 wt. %, and preferably greater than 1 wt. % (calculated as the promoting metal), based on the amount of arylmetallo carboxylate charged to the reaction liquid. Use of greater than 20 wt. % promoter in the reaction liquid will generally not be necessary.

The effluent from the reaction vessel can be treated by conventional means, such as distillation, crystallization, and the like, to recover the desired aryl carboxylate product therefrom.

Alternatively, after removal of the aryl iodide and metallo acetate by-products, the aryl carboxylate can then be contacted with water or another source of a hydroxy group to form the corresponding phenol from the aryl carboxylate. Thus, phenyl acetate can be contacted with water to form phenol.

The process of this invention can be further illustrated by reference to the following Examples wherein parts are by weight unless otherwise indicated.

EXAMPLE 1

To a round bottom glass flask is added 5 mmols of phenyl mercuric acetate, 5 mmols of phenyl iodoso diacetate and 20 ml. of acetic acid as solvent. The resulting liquid mixture is stirred employing a magnetic stirrer and heated by means of an oil bath to a temperature of about 75° C. for a period of about 4 hours. The flask is open to the atmosphere during the experiment. At the end of the 4 hours of reaction, the liquid mixture in the flask is analyzed by gas chromatography. Phenyl mercuric acetate conversion is found to be 70%, and phenyl acetate is found to be produced in a selectivity of about 49%, corresponding to a phenyl acetate yield of about 34%, based on phenyl mercuric acetate charged.

EXAMPLE 2

The procedure of Example 1 is repeated except that 1.0 mmols of cupric acetate is also charged to the flask. After the 4 hours of reaction at a temperature of 75° C., phenyl acetate yield is found to be about 50%, based on phenyl mercuric acetate charged, at a phenyl mercuric acetate conversion of about 73% and a phenyl acetate selectivity of about 68.5%. This illustrates the promoting effect of cupric acetate for the reaction.

EXAMPLE 3

The procedure of Example 2 is repeated except that 2.0 mmols of cupric acetate are charged to the reaction vessel, and the reaction is carried out for 0.25 hour at 120° C. At the end of this time, phenyl acetate yield is found to be about 48%, at a phenyl mercuric acetate conversion of about 64% and a phenyl acetate selectivity of about 75%.

EXAMPLE 4

The procedure of Example 3 is repeated except that only 10 ml. of acetic acid is charged to the reaction vessel, thereby increasing the concentration of the phenyl mercuric acetate and phenyl iodoso diacetate reactants in the liquid. At the end of the 0.25 hour of reaction at 120° C., phenyl acetate yield is found to be increased to 68%, at a phenyl mercuric acetate conversion of about 72% and a phenyl acetate selectivity of about 94%.

EXAMPLE 5

The procedure of Example 4 is repeated except that a reaction time of 4 hours at a temperature of 100° C. is employed. Phenyl acetate is found to be produced in a yield of about 86% and a selectivity of about 93%, at a phenyl mercuric acetate conversion of about 92%.

EXAMPLE 6

Following the procedure of Example 1, 5 mmols of triphenyl tin acetate, 15 mmols of phenyl iodoso diacetate and 2.0 mmols of cupric acetate, together with 20 ml. of acetic acid are charged to the reaction vessel. After 4 hours of reaction at 100° C. phenyl acetate is found to be produced in a yield of about 66% and a selectivity of about 72%, at a triphenyl tin acetate conversion of about 92%.

EXAMPLE 7 FOR COMPARISON

Example 1 is repeated in a series of runs employing either sodium acetate or pyridine in the reaction zone, to illustrate the adverse effects of these basic compounds upon the desired formation of phenyl acetate.

In a first run, the charge to the reaction vessel consists of 5 mmols phenyl mercuric acetate, 5 mmols phenyl iodoso diacetate and 2.0 mmols sodium acetate, together with 20 ml. of acetic acid. After 4 hours of reaction at 75° C. phenyl acetate is produced in a yield of only 8% and in a 22% selectivity, at a phenyl mercuric acetate conversion of only 36%.

In a second run, the charge to the reaction vessel is 5 mmols phenyl mercuric acetate, 5 mmols of phenyl iodoso diacetate, 15 ml of acetic acid and 5 ml. of pyridine. After 4 hours of reaction at 75° C., no detectable phenyl acetate is found in the reaction mixture.

It will be obvious that various changes and modifications can be made without departing from the invention, and it is intended, therefore, that all matter contained in the foregoing description shall be interpreted as illustrative only and not as limitative of the invention.

I claim:

1. A process for preparing an aryl carboxylate which comprises contacting (1) an arylmetallo carboxylate selected from the group consisting of compunds having the formula:

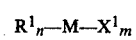

wherein $R^1$ is as defined below; M is a metal cation in its highest oxidation state selected from the group consisting of Hg, Sn, Tl, Pb and Cd; $X^1$ is a carboxylate group of from 2 to 20 carbon atoms derived from an aliphatic or aromatic mono- or di-carboxylic acid; and n and m are each integers of from 1 to $(t-1)$, wherein t is the valence of the metal cation, with the proviso that $n+m=t$, with (2) at least one aryliodoso carboxylate selected from the group consisting of compounds of the formula:

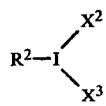

wherein $R^2$ is as defined below, $X^2$ and $X^3$ are the same or different and are each carboxyl groups derived from aliphatic saturated or aromatic monocarboxylic acids having from 2 to 20 carbon atoms, or from aliphatic saturated or aromatic di-carboxylic acids having from 2 to 20 carbon atoms, $R^1$ and $R^2$ being the same or different and being selected from the group consisting of substituted or unsubstituted mono- or polynuclear aryl moieties of 6–18 carbon atoms, the substituents, if present, being selected from the group consisting of alkyl of 1 to 12 carbon atoms, cycloalkyl of 4 to 12 carbon atoms, and heterocyclic having from 6 to 10 member rings containing one or more O or S ring atoms, cyano, keto, having from 2 to 10 carbon atoms, carboxylate having from 1 to 10 carbon atoms and carboalkoxy having from 2 to 10 carbon atoms, said contacting being in liquid medium and at elevated temperature to form the corresponding aryl carboxylate.

2. The process according to claim 1 wherein the liquid medium is maintained at a temperature of from about 25° to 150° C.

3. The process according to claim 1 wherein the arylmetallo carboxylate and aryliodoso carboxylate are each employed in the concentration such that the sum of their concentrations is at least 0.05 moles per liter of reaction medium.

4. The process according to claim 1 wherein the liquid medium additionally contains an effective amount of at least one metal salt promoter selected from the group consisting of inorganic and organic salts of Cu, Co, Fe and Mn, and mixtures thereof, said salt being at least partially soluble in the liquid reaction medium.

5. The process according to claim 4 wherein said promoter is employed in an amount of at least about 0.1 wt. %, calculated as the promoting metal, based on the amount of arylmetallo carboxylate charged to the liquid medium.

6. The process according to claim 1 wherein the $R^1$ and $R^2$ aryl groups are the same and are phenyl, naphthyl, or 2-, 3-, or 4-isopropylphenyl, and wherein the $X^1$, $X^2$ and $X^3$ groups are the same or different and are independently selected from the group consisting of aliphatic monocarboxylic acids having from 2 to 6 carbon atoms.

7. The process according to claim 1 wherein the arylmetallo carboxylate and aryliodoso carboxylate are contacted in the molar ratio of from about 10:1 to 1:10.

* * * * *